United States Patent [19]

Bernstein

[11] Patent Number: 5,310,342
[45] Date of Patent: May 10, 1994

[54] ROTARY TOOL FOR SHAPING REPLACEMENT TEETH

[76] Inventor: Stuart H. Bernstein, 24 Cummings Rd., Newton, Mass. 02159

[21] Appl. No.: 19,620

[22] Filed: Feb. 19, 1993

[51] Int. Cl.$^5$ ............................................. A61C 3/06
[52] U.S. Cl. ................................. 433/166; 51/206 R; 51/395; 51/398
[58] Field of Search ........................ 433/125, 165, 166; 51/395, 396, 398, 407, 206 R, 209 R

[56] References Cited

U.S. PATENT DOCUMENTS

| | | | |
|---|---|---|---|
| 494,471 | 3/1893 | Gardner | 51/206 R |
| 2,685,738 | 8/1954 | Leff | 433/166 |
| 2,768,483 | 10/1956 | Hurst | 51/293 |
| 2,793,438 | 5/1957 | Ashkin | 433/166 |
| 2,842,844 | 7/1958 | Seal | 433/166 |
| 2,877,105 | 3/1959 | Smith | 51/206 R |
| 2,997,820 | 8/1961 | Skoog | 51/209 R |
| 3,259,959 | 7/1966 | Tobey | 51/206 R |
| 3,495,362 | 3/1967 | Hillenbrand | 51/395 |
| 3,869,263 | 3/1975 | Greenspan | 51/395 |

OTHER PUBLICATIONS

Zahn Dental Company Incorporated, 1991-1992 Catalog pp. 89-90.
Denerica Catalog, 1991-1992, p. 102 and additional pages.

Primary Examiner—John J. Wilson
Attorney, Agent, or Firm—Fish & Richardson

[57] ABSTRACT

A rotary member for shaping replacement teeth including a metal support having a generally circular outer shape with a radius less than 20 mm, the metal support having a generally flat inner portion extending at least 30% of the radius, the metal support also having contoured contact surfaces located radially outward of the flat inner portion, and abrasive particles bonded to the contoured contact surfaces.

8 Claims, 1 Drawing Sheet

ROTARY TOOL FOR SHAPING REPLACEMENT TEETH

BACKGROUND OF THE INVENTION

The invention relates to rotary members for shaping replacement teeth.

When making metal and porcelain replacement teeth, dental technicians perform a shaping procedure using rotary dental tools. The tools typically have flat metal discs with diamond abrasive surfaces, and some discs are flexible in order to bend to permit the dental technician to contour the replacement teeth surfaces.

SUMMARY OF THE INVENTION

The invention features, in general, a rotary member for shaping replacement piece that includes a metal support with a generally circular outer shape and abrasive particles bonded thereon on contoured contact surfaces. The metal support has a radius less than about 20 mm and has a generally flat inner portion extending to at least 30% of the radius, and the contoured contact surfaces are located radially outward of the flat inner portion. This design permits dental technicians to better shape contours on the teeth, particularly when the contours need to be provided on hard-to-reach places, such as between adjacent teeth.

In preferred embodiments, the contoured contact surfaces are arcuate, and in particular are semicircular in shape in cross-section, extending away from and back to a plane passing through the flat inner portion. The metal support has a lip that is located outside of the arcuate area and has abrasive particles on both sides. The flat inner portion has a radius between 4 mm and 6 mm (preferably about 5.5 mm); the arcuate portion has a depth between 0.7 mm and 2.3 mm (preferably between 1.3 mm and 1.7 mm, and most preferably about 1.5 mm) and a width, in section, between 1.4 mm and 4.6 mm (preferably between 2.6 mm and 3.4 mm, and most preferably about 3.0 mm); and the lip has a width between 0.2 mm and 1.8 mm (preferably between 0.8 mm and 1.5 mm, and most preferably about 1.0 mm) wide. The metal support is made out of stamped stainless steel 0.02 mm to 1.0 mm thick, preferably between 0.08 mm and 0.15 mm (most preferably about 0.1 mm). The abrasive particles preferably are diamond particles. Alternatively, the contoured contact surfaces could have the shape of a portion of a cone and could be on a portion of the metal support that has a V-shape in cross-section.

Other advantages and features of the invention will be apparent from the following description of the preferred embodiments thereof and from the claims.

DESCRIPTION OF THE PREFERRED EMBODIMENTS

The drawings will be described first.

Drawings

STRUCTURE

Figure 1:
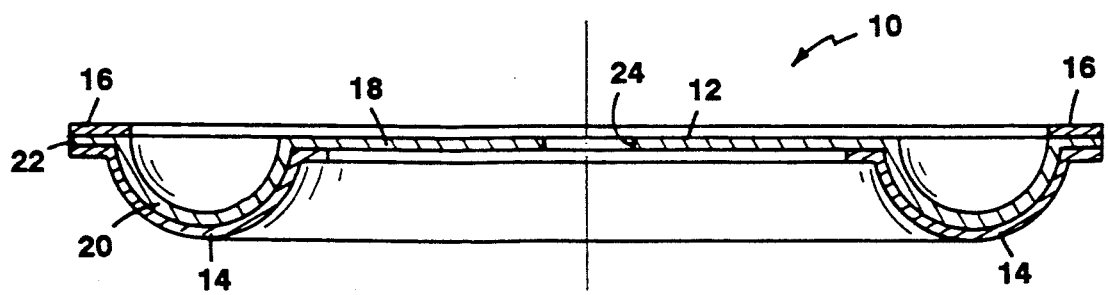
FIG. 1 is a vertical sectional view of a rotary member for shaping replacement teeth according to the invention.

Referring to FIG. 1, there is shown rotary member 10 for shaping metal or porcelain replacement teeth. It includes metal support 12 and coatings 14, 16 of abrasive diamond particles on outer portions thereof. Metal support 12 has a generally flat inner portion 18 and contoured portion 20 radially outward thereof. Support 12 has a circular outer shape with a radius less than 20 mm, preferably less than 15 mm, and most preferably less than 12 mm, and, in a most preferred embodiment described herein, about 9.5 mm. Generally flat inner portion extends at least 30% of the overall radius and preferably has a radius between 4 mm and 6 mm and most preferably about 5 mm. Contoured portion 20 has a semicircular shape in cross-section and has a width of 3.0 mm and a depth of 1.5 mm. The depth could be between 0.7 mm and 2.3 mm (preferably between 1.3 mm and 1.7 mm), and the width could be between 1.4 mm and 4.6 mm (preferably between 2.6 and 3.4 mm). There is a 1.0 mm wide outer lip 22 beyond arcuate portion 20; lip 22 could be between 0.2 mm and 1.8 mm wide (preferably between 0.8 mm and 1.5 mm).

Metal support 12 is made from 1.0 mm thick stainless steel that is stamped into the shape shown in FIG. 1. Other thicknesses (e.g., between 0.02 mm and 1.0 mm, preferably between 0.08 mm and 0.15 mm) and materials could be used, depending upon the desired flexibility.

Figure 3:
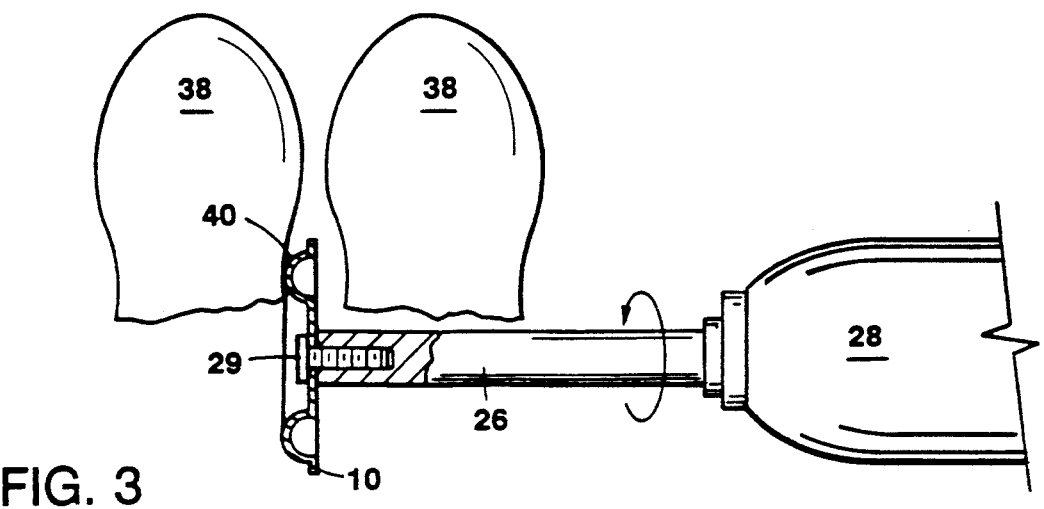
FIG. 3 is a diagrammatic elevation, partially in section and partially broken away, showing the FIG. 1 rotary member on a hand-held tool used to shape replacement piece.

Referring to FIGS. 1 and 3, central hole 24 is used for mounting rotary member 10 on rotating shaft 26 supported by handle 28 of a rotary drive. Rotary member 10 is held on shaft 26 via screw 30.

Diamond particle coatings 14, 16 are painted on with a nickel paste and adhered to the metal support via electroplating. The particles can be "course" "or fine" particles, terms defining sizes well known in the industry, to provide different shaping characteristics.

Figure 2:
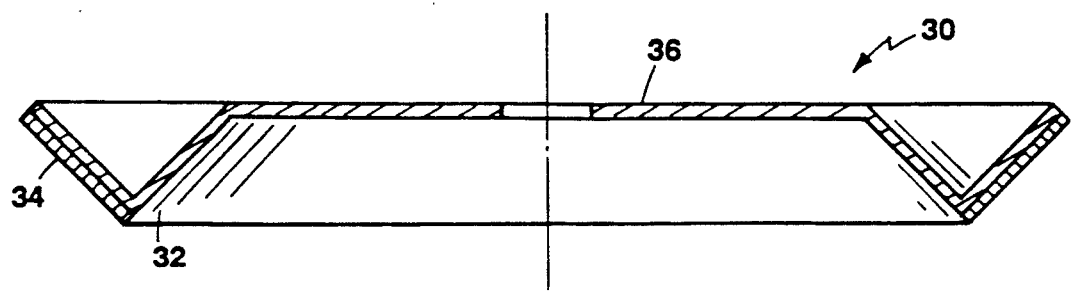
FIG. 2 is a vertical sectional view of an alternative rotary member.

FIG. 2 shows rotary member 30, which is similar to rotary member 10 except that it has a contoured contact portion 32 that has a V-shape in cross-section and has diamond particle layers 34 on the outer leg of the V. The legs of the V make a 45, angle with the plane of flat portion 36. This angle could vary between 30° and 60°.

Operation

Referring to FIG. 3, in use, rotary member 10 or 30 is attached to shaft 26 via screw 30 and is used to shape replacement teeth 38. The contoured nature of contoured portion 20 permits the dental technician to provide contours at surfaces 40 between teeth that would otherwise be difficult to achieve. The operator applies a generally axial force along shaft 26, and rotary member 10 or 30 gives and bends back where it contacts the tooth (e.g., up to 45°), owing to the flexible nature of the metal disc from which it is made. Metal support 12 could be made from thinner metal to provide relatively more flex or from thicker metal to provide relatively less flex and permit more force to be applied at less flex.

Other Embodiments

Other embodiments of the invention are within the scope of the appended claims.

What is claimed is:

1. A rotary member for shaping replacement teeth comprising
    a metal support having a generally circular outer shape with a radius less than 20 mm, said metal support having a generally flat inner portion extending at least 30% of said radius, said metal support also having contoured contact surfaces located radially outward of said flat inner portion, and abrasive particles bonded to said contoured contact surfaces, wherein said contoured contact surfaces are arcuate, wherein said contoured contact surfaces are semicircular in shape in cross-section and extend away from and back to a plane passing through said generally flat inner portion.

2. The rotary member of claim 1 wherein said metal support has a lip outside of the contoured contact surfaces.

3. The rotary member of claim 1 wherein said flat inner portion has a radius between 4 mm and 6 mm, said semicircular contoured contact surfaces are on a semicircular portion of said metal support having a depth between 0.7 mm and 2.3 mm and a width between 1.4 mm and 4.6 mm.

4. The rotary member of claim 3 wherein said metal support has a lip outside of said contoured contact surfaces, and said lip is between 0.2 mm and 1.8 mm wide.

5. The rotary member of claim 4 wherein said is between 1.3 mm and 1.7 mm, and said width of said semicircular portion is between 2.6 mm and 3.4 mm.

6. The rotary member for shaping replacement teeth comprising a metal support having a generally circular outer shape with a radius less than 20 mm, said metal support having a generally flat inner portion extending at least 30% of said radius, said metal support also having contoured contact surfaces located radially outward of said flat inner portion, and abrasive particles bonded to said contoured contact surfaces, wherein said contoured contact surface has the shape of a portion of a cone and is on a portion of said metal support that has a V shape in cross-section.

7. The rotary member for shaping replacement teeth comprising a metal support having a generally circular outer shape with a radius less than 20 mm, said metal support having a generally flat inner portion extending at least 30% of said radius, said metal support also having contoured contact surfaces located radially outward of said flat inner portion, and abrasive particles bonded to said contoured contact surfaces, wherein said metal support is made from stamped stainless steel between 0.8 mm and 0.15 mm in thickness, wherein said metal support is sufficiently flexible to bend such that a line through the circumference and the center of the rotary member makes an angle of 45° with the unflexed position under the application of hand applied force when mounted on a rotary shaft extending from a handheld handle.

8. The rotary member for shaping replacement teeth comprising a metal support having a generally circular outer shape with a radius less than 20 mm, said metal support having a generally flat inner portion extending at least 30% of said radius, said metal support also having contoured contact surfaces located radially outward of said flat inner portion, and abrasive particles bonded to said contoured contact surfaces, wherein said contoured contact surfaces are arcuate, wherein said contoured contact surfaces are semicircular in shape in cross-section and extend away from and back to a plane passing through said generally flat inner portion, wherein said flat inner portion has a radius between 4 mm and 6 mm, said semiconductor contoured contact surfaces are on a semiconductor portion of said metal support having a depth between 0.7 mm and 2.3 mm and a width between 1.4 mm and 4.6 mm, wherein said metal support has a lip outside of said contoured contact surfaces, and said lip is between 0.2 mm and 1.8 mm wide wherein there are abrasive particles carried on both sides of said lip.

* * * * *